(12) United States Patent
Freiburger et al.

(10) Patent No.: US 6,511,465 B1
(45) Date of Patent: *Jan. 28, 2003

(54) ABSORBENT ARTICLE HAVING A REFASTENABLE MECHANISM

(75) Inventors: Sarah Jane Marie Freiburger, Kaukauna, WI (US); Mary Anne Bruemmer-Prestley, Appleton, WI (US); Nefetari Edris Bordain, Dunwoody, GA (US); Suzanne Marie Schmoker, Oshkosh, WI (US); David Arthur Fell, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 43 days.

This patent is subject to a terminal disclaimer.

(21) Appl. No.: 09/637,425

(22) Filed: Aug. 11, 2000

Related U.S. Application Data

(60) Provisional application No. 60/150,258, filed on Aug. 23, 1999.

(51) Int. Cl.⁷ ............................................. A61F 13/15
(52) U.S. Cl. ........................... 604/385.29; 604/385.01; 604/391
(58) Field of Search ..................... 604/385.01, 385.24, 604/385.27–385.29, 391, 392, 396

(56) References Cited

U.S. PATENT DOCUMENTS

| | | | |
|---|---|---|---|
| 4,205,679 A | 6/1980 | Repke et al. | |
| 4,573,987 A | 3/1986 | Lamb, Jr. | |
| 4,699,621 A | 10/1987 | Stevens et al. | |
| 4,747,846 A | 5/1988 | Boland et al. | |
| 4,834,736 A | 5/1989 | Boland et al. | |
| 4,906,243 A | 3/1990 | Dravland | |
| 5,370,634 A | * 12/1994 | Ando et al. | 604/358 |
| 5,527,302 A | * 6/1996 | Endres et al. | 604/382 |
| 5,745,922 A | 5/1998 | Rajala et al. | |

(List continued on next page.)

FOREIGN PATENT DOCUMENTS

| | | |
|---|---|---|
| DE | 197 32 551 A1 | 2/1999 |
| EP | 0 321 985 A2 | 6/1989 |
| EP | 0 412 579 A1 | 2/1991 |

(List continued on next page.)

Primary Examiner—Aaron J. Lewis
Assistant Examiner—Jamisue A Webb
(74) Attorney, Agent, or Firm—Thomas J. Connelly; Scott A. Baum

(57) ABSTRACT

A disposable absorbent article is disclosed having a front portion, a back portion and a crotch portion. The crotch portion joins the front portion to the back portion. The back portion has a first end and a second end. The back portion is divided into a first section and a second section. The first section is extendable in a transverse direction and has a length $L_2$ measured perpendicularly from the first end of the back portion to a line drawn parallel thereto. The second section has a length $L_3$ measured perpendicularly from the second end of the back portion to the line drawn parallel to the first end. The second section has a first side edge, a second side edge, a first area $A_1$ and a second area $A_2$. The first area $A_1$ represents an area bounded by the first and second side edges, the second end, and the line drawn parallel to the first end. The second area $A_2$ represents an area bounded by first and second lines, the second end, and the line drawn parallel to the first end. The first and second lines are drawn perpendicular to the second end at points where the first and second side edges intersect the second end. The first and second lines intersect the line drawn parallel to the first end. The second section has a ratio $A_1/A_2$ which ranges from between about 1.3 to about 3.5. First and second fasteners are secured to the back portion. An absorbent is secured to at least one of the front, back or crotch portions. Each of the first and second fasteners are releasably attached to the front portion to form a pant-like article having a waist opening and a pair of leg openings.

20 Claims, 5 Drawing Sheets

U.S. PATENT DOCUMENTS

| | | | |
|---|---|---|---|
| 5,817,087 A | * 10/1998 | Takabayashi et al. | 604/385.29 |
| 5,957,908 A | * 9/1999 | Kline et al. | 604/386 |
| 6,098,203 A | 8/2000 | Rajala et al. | |
| 6,110,157 A | * 8/2000 | Schmidt | 604/385.01 |
| 6,142,986 A | 11/2000 | Lord et al. | |
| 6,312,420 B1 | 11/2001 | Sasaki et al. | |

FOREIGN PATENT DOCUMENTS

| | | |
|---|---|---|
| EP | 0 433 951 A2 | 6/1991 |
| EP | 0 450 541 A2 | 10/1991 |
| EP | 0 682 928 A1 | 11/1995 |
| FR | 2 443 831 | 7/1980 |
| GB | 2 244 422 A | 12/1991 |
| GB | 2 288 313 A | 10/1995 |
| GB | 2 294 865 A | 5/1996 |
| GB | 2 308 290 A | 6/1997 |
| WO | WO 95/00096 | 1/1995 |
| WO | WO 96/11657 | 4/1996 |
| WO | WO 97/22318 | 6/1997 |
| WO | WO 97/36566 | 10/1997 |

* cited by examiner

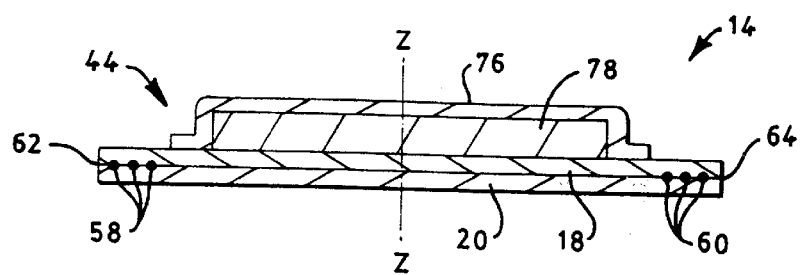
FIG. 7
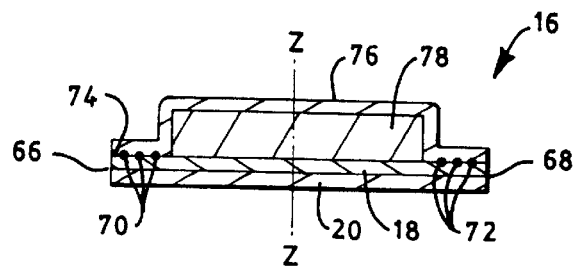
FIG. 8
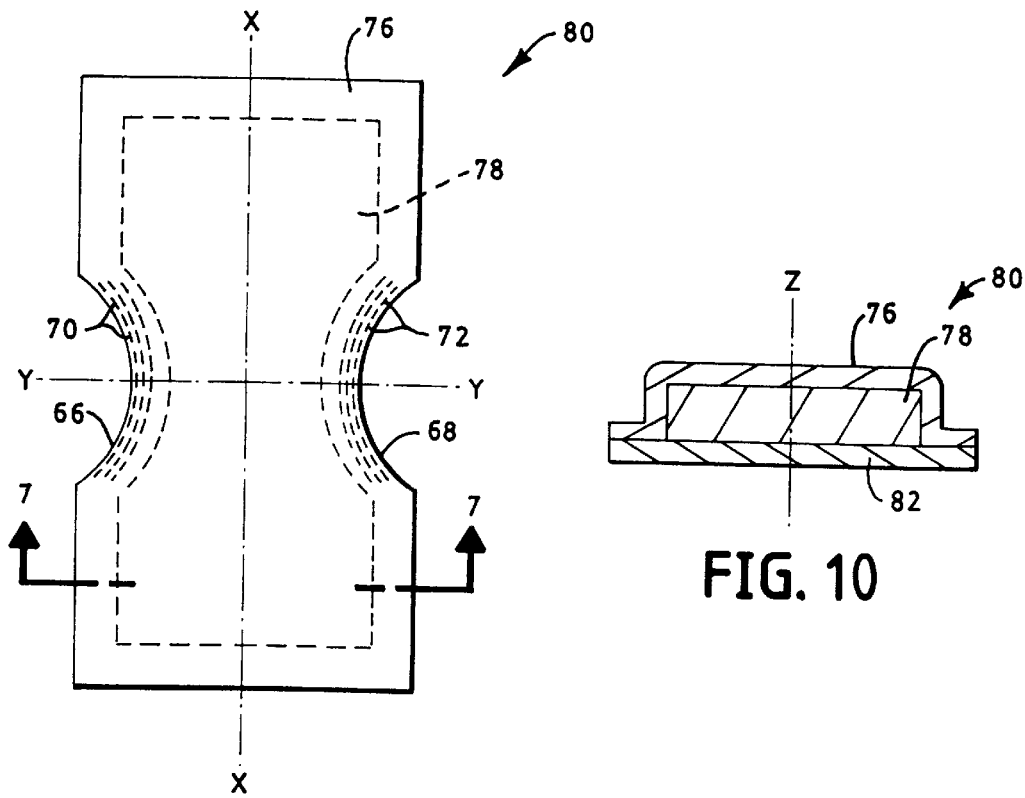
FIG. 9
FIG. 10

ABSORBENT ARTICLE HAVING A REFASTENABLE MECHANISM

This application claims priority from presently copending U.S. Provisional Application No. 60/150,258 entitled "DISPOSABLE ABSORBENT ARTICLE HAVING IMPROVED FIT AND BODY COVERAGE" and filed on Aug. 23, 1999, in the name of Sarah Jane Marie Freiburger et al.

FIELD OF THE INVENTION

This invention relates to an absorbent article having a refastenable mechanism. More specifically, this invention relates to a disposable absorbent article having a refastenable mechanism that improves body fit and reduces the likelihood of fluid leakage.

BACKGROUND OF THE INVENTION

Today, various disposable absorbent articles exist which are designed to absorb and retain body fluid and/or excrement. Examples of such articles include incontinence products such as pants, briefs and undergarments, baby diapers, feminine care menstrual pants, training pants, etc. While most of these articles perform satisfactorily for their intended purpose, some are difficult to remove from the body of the wearer. Many do not have a refastenable mechanism that allows the article to be easily adjusted during use or be easily removed from the wearer's body before the product is permanently descarded while maintaining an underwear like fit. Some of today's commercially available products do not conform well to the human body and this poor fit increases the likelihood of fluid leakage while the product is being worn. Therefore, there remains a need for a disposable absorbent article having a refastenable mechanism that will produce improved fit to the human body and reduce the likelihood of fluid leakage.

Now, a disposable absorbent article has been invented which has a refastenable mechanism that improves body fit and reduces the likelihood of fluid leakage.

SUMMARY OF THE INVENTION

Briefly, this invention relates to an absorbent article having a refastenable mechanism. The absorbent article has a front portion, a back portion and a crotch portion. The crotch portion connects the front portion to the back portion. The back portion has a first end, a second end and first and second side edges. The back portion is divided into a first section and a second section. The first section is extendable in at least one direction and has a length $L_2$ measured perpendicularly from the first end of the back portion to a line drawn parallel thereto. The second section has a length $L_3$ measured perpendicularly from the second end of the back portion to the line drawn parallel to the first end whereby a ratio $L_2/L_3$ is established which ranges from between about 0.1 to about 2. First and second fasteners are positioned adjacent to one of the first and second side edges of the back portion and are secured thereto. The absorbent article further includes an absorbent secured to at least one of said front, back or crotch portions. Each of the first and second fasteners are releasably attached to the front portion to form a pant-like article having a waist opening and a pair of leg openings.

The general object of this invention is to provide an absorbent article having a refastenable mechanism. A more specific object of this invention is to provide a disposable absorbent article having a refastenable mechanism that improves body fit and reduces the likelihood of fluid leakage.

Another object of this invention is to provide an absorbent article having a refastenable mechanism that is easy to manufacture, is relatively inexpensive and is easy to use.

Still another object of this invention is to provide an absorbent article that can easily be adjusted to conform to a wearer's body.

Other objects and advantages of the present invention will become more apparent to those skilled in the art in view of the following description and the accompanying drawings.

BRIEF DESCRIPTION OF THE DRAWINGS

FIG. 7 is a cross-sectional view of FIG. 1 taken along the line 7—7.

FIG. 8 is a cross-sectional view of FIG. 1 taken along the line 8—8.

FIG. 9 is a top view of an alternative absorbent assembly.

FIG. 10 is a cross-sectional view of FIG. 9 taken along line 10—10.

DETAILED DESCRIPTION OF THE PREFERRED EMBODIMENTS

Figure 1:
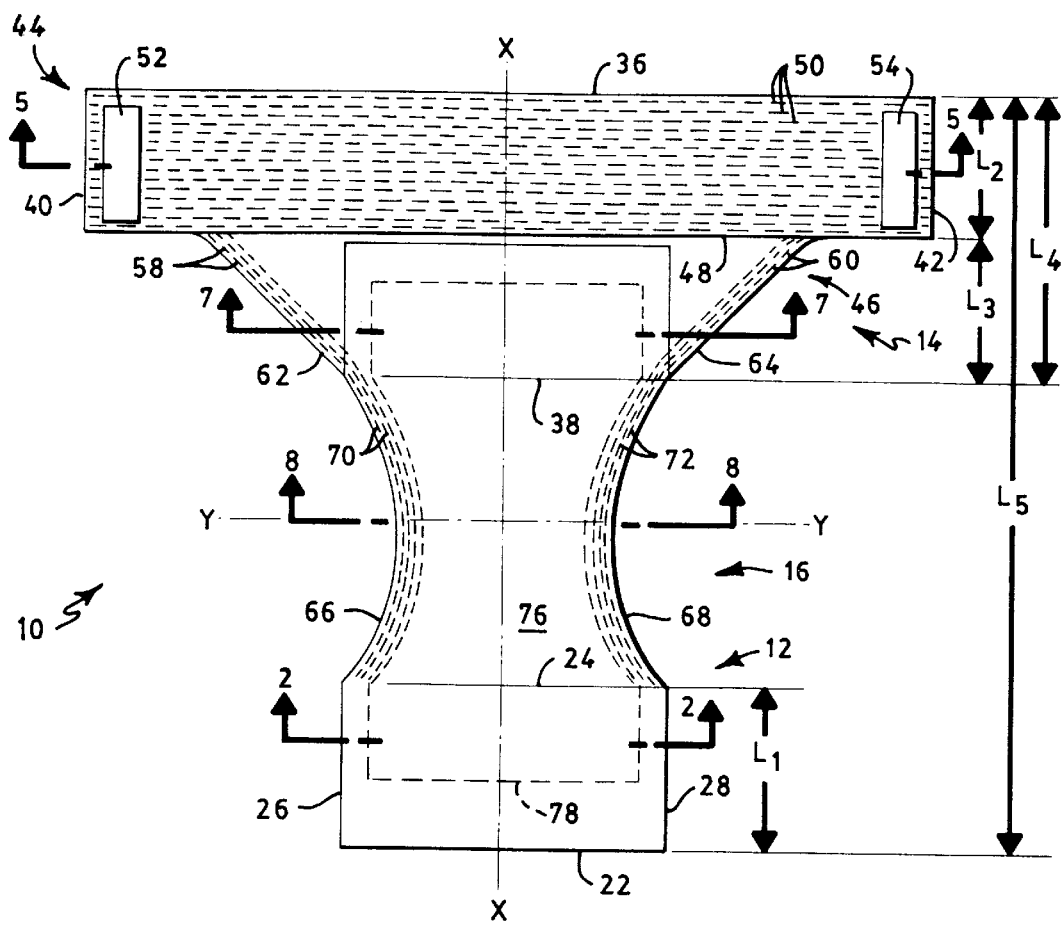
FIG. 1 is a top plane view of an absorbent article having a refastenable mechanism and shown in a pre-assembled flat configuration.
Figure 2:
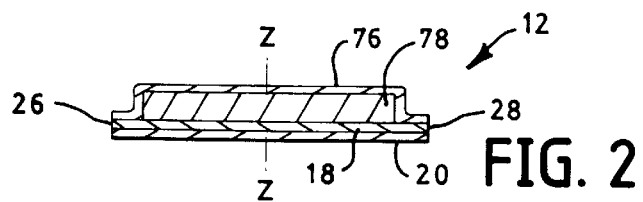
FIG. 2 is a cross-sectional view of FIG. 1 taken along line 2—2.

Referring to FIGS. 1 and 2, a disposable absorbent article 10 having a refastenable mechanism is shown. The absorbent article 10 has a longitudinal central axis X—X, a transverse central axis Y—Y and a vertical central axis Z—Z. The absorbent article 10 includes a front portion 12, a back portion 14 and a crotch portion 16. The crotch portion 16 connects the front portion 12 to the back portion 14. The front, back and crotch portions 12, 14 and 16 can be formed from a single piece of material or from two or more pieces of material. Each of the front, back and crotch portions 12, 14 and 16 can be a single layer of material or each can be formed as a laminate having two or more layers. In FIG. 2, the front portion 12 is shown as a laminate having an upper layer 18 and a lower exterior layer 20. Preferably, the front, back and crotch portions 12, 14 and 16, respectively, are formed as a laminate having two layers.

When a laminate is utilized, the upper layer 18 faces toward the body of the wearer in use and can be either liquid permeable or liquid-impermeable. A thermoplastic film can be used to make the upper layer 18 liquid-impermeable. The lower layer 20 faces away from the body of the wearer in use and it too can either be liquid permeable or liquid-impermeable. Preferably, the lower layer 20 is liquid permeable and is formed from a soft material such as a non-woven. Spunbond is a non-woven material manufactured by Kimberly-Clark Corporation that is soft and pliable and functions well as the lower layer 20. It is beneficial to make one of the layers 18 or 20 liquid-impermeable in the crotch portion 16 so as to prevent body fluid absorbed by the absorbent article 10 from exiting.

The front portion 12, which will be aligned around a portion of the front torso of a wearer's body in use, includes a first end 22, a second end 24, a first side edge 26 and a second side edge 28. The front portion 12 can be constructed such that its lower layer 20 is formed from a material that has fastening qualities. For example, the lower layer 20 can be formed from either a hook material or a loop material. The entire front portion 12 can then act as a fastening element and be releasably attached to another member or have another member releasably attached to it. The front portion 12 can also be formed from other materials that have the ability to releasably attach to another member. The lower layer 20 can be an adhesive layer, a co-adhesive layer or have some other properties that allow it to be releasably fastened to another member.

Figure 3:
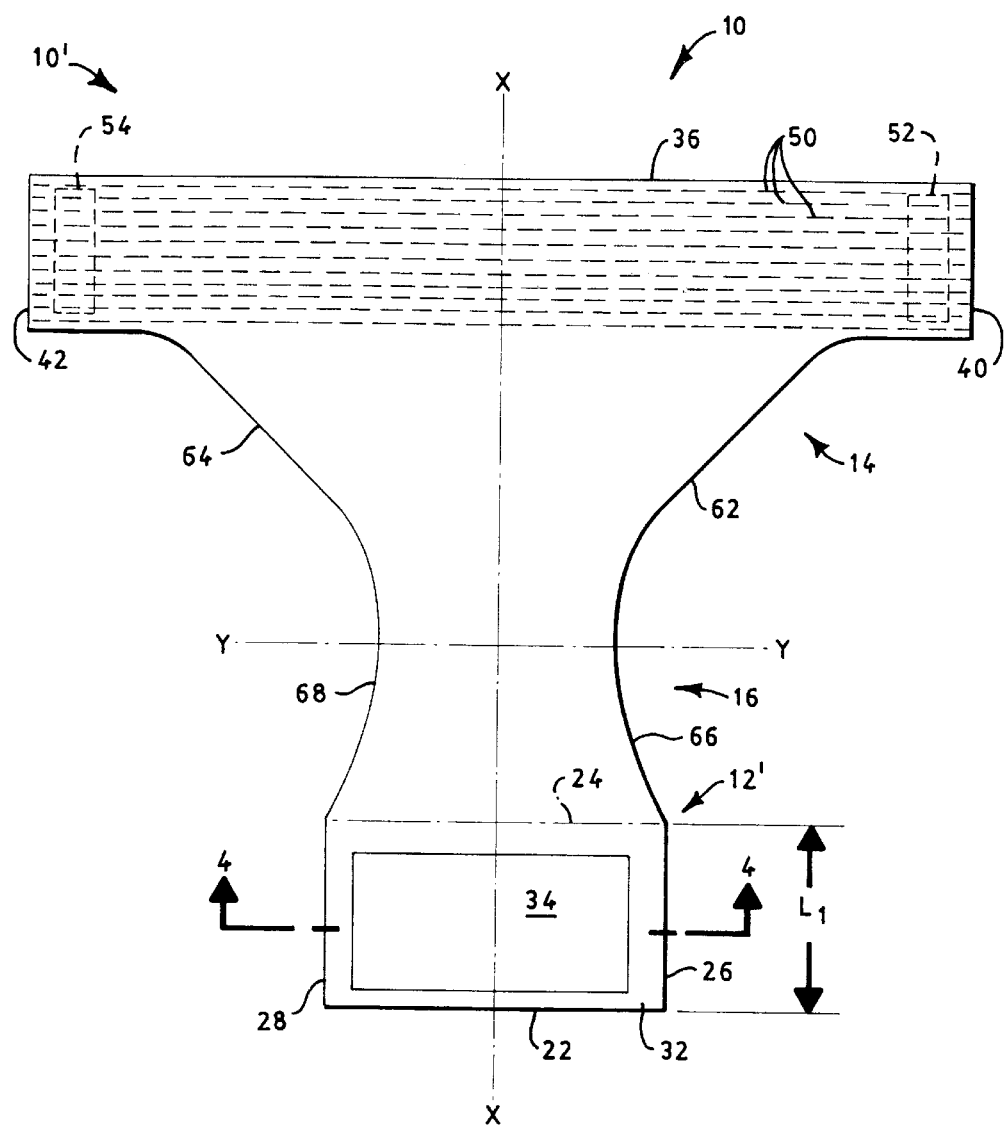
FIG. 3 is a bottom view of an absorbent article showing an alternative embodiment for the fastening mechanism on the front portion.
Figure 4:
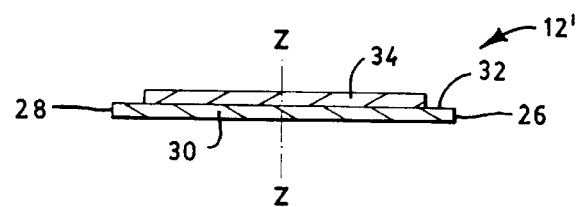
FIG. 4 is a cross-sectional view of FIG. 3 taken along line 4—4.

Referring to FIGS. 3 and 4, a bottom view of the absorbent article 10 showing an alternative embodiment for the fastening mechanism on the front portion 12. For ease of understanding, the same numerals will be used in FIGS. 3 and 4 as were used in FIGS. 1 and 2 except for the use of prime numbers for the front portion 12'. The front portion 12' of the absorbent article 10' is formed as a single layer 30 having a surface 32. The surface 32 faces away from the body of the wearer during use. Secured to the surface 32 is a fastener 34. The fastener 34 can be a separate piece or patch of material or it can include two or more distinct pieces. The fastener 34 is a "releasable fastener" having the ability to fasten onto another member or have another member fasten onto it. A "releasable fastener" is one that will permit two members to be fastened and then unfastened multiple times. A "releasable fastener" differs from a "permanent fastener" in that it does not require the bond to be permanently destroyed once the connection is broken. The fastener 34 can be formed from a hook material or from a loop material. The fastener 34 can also be formed from an adhesive, a co-adhesive or from some other kind of material that will allow for a releasable attachment or connection to occur with another member. The purpose of the fastener 34 will be explained shortly.

Returning again to the FIG. 1, the front portion 12 has a length $L_1$. The length $L_1$ is measured parallel to the longitudinal central axis X—X. The length $L_1$ should be equal to or greater than about 1 inches (about 2.5 cm).

Figure 5:
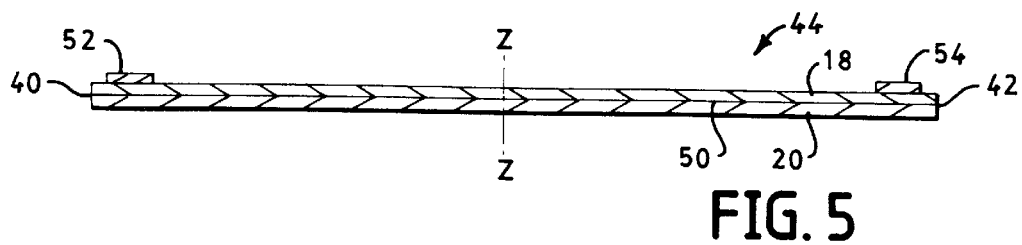
FIG. 5 is a cross-sectional view of FIG. 1 taken along the line 5—5.

Referring now to FIGS. 1 and 5, the absorbent article 10 also includes the back portion 14 that will contact the back and sides of a wearer's torso in use. The back portion 14 has a first end 36, a second end 38, and first and second side edges 40 and 42, respectively. The back portion 14 is depicted as a laminate, identical to that used to form the front portion 12. The laminate includes the upper layer 18 which faces the body of the wearer during use and the lower exterior layer 20 which faces away from the wearer's body during use. The upper layer 18 can be either liquid permeable or liquid-impermeable. Preferably, the upper layer 18 is liquid permeable.

The back portion 14 is divided into a first section 44 and a second section 46. The first section 44 has a length $L_2$ measured perpendicularly from the first end 36 to a line 48 drawn parallel thereto. The length $L_2$ should be equal to or greater than about 2 inches (about 5 cm). Preferably, for an adult size garment, the length $L_1$ should range from between about 3 inches to about 7 inches (about 7.6 cm to about 18 cm). Most preferably, for an adult size garment, the length $L_1$ should range from between about 6 inches to about 7 inches (about 15 cm to about 18 cm). The significance of the dimension $L_1$ will be explained shortly.

The first section 44 of the back portion 14 should be extendable in the transverse direction so that it can easily stretch to accommodate the anatomy of the wearer's torso. The "transverse direction" is a direction parallel to the transverse central axis Y—Y of the absorbent article 10. The first section 44 can also be extendable in the X—X and/or Z—Z directions if desired. The first section 44 can be made to be extendable in a number of ways. One way is to construct the first section 44 into gathers, pleats or undulations such that as one pulls on the first and second side edges 40 and 42, respectively, the first section 44 extends in the transverse direction. Another way to make the first section 44 extendable is to form it from an elastic material, an elastic composite or construct it to contain elastic. The first section 44 could also be formed from a material having elastic properties and characteristics. Preferably, the first section 44 will be able to stretch and retract like a rubber band. The first section 44 should be capable of extending and retracting multiple times. This ability to extend and retract will allow the refastening mechanism of the absorbent article 10 to be adjusted whenever needed by the wearer.

The first section 44 will exhibit elastic properties if it is formed from a material such as "stretch bonded laminate". A "stretch bonded laminate" is a material that can be used to form the first section 44. Stretch bonded laminate is a material manufactured by Kimberly-Clark Corporation having an office at 401 North Lake Street, Neenah, Wis. 54956. Other elastic materials or materials exhibiting elastic properties or characteristics can also be used. Such materials are known to those skilled in the art.

Another way of making the first section 44 elastic is to position and bond one or more elongated elastic strands 50 between the upper and lower layers 18 and 20, respectively. By sandwiching multiple elastic strands 50 between the upper and lower layers 18 and 20, one can adjust the amount of stretch imparted into the first section 44. In FIG. 1, multiple elastic strands 50 are shown. There can be from between about 2 to about 100 elastic strands 50 present in the first section 44. Preferably, there are from between about 10 to about 50 elastic strands 50 present in the first section 50. Most preferably, there are from between about 15 to about 25 elastic strands present in the first section 44. The elastic strands 50 can be in the form of elongated strands, ribbons, bands, strips, etc. The cross-sectional configuration of the elastic strands 50 can vary. The cross-section of the elastic strands 50 can be circular, square, rectangular, oval, etc. The elastics strands 50 preferably will extend transversely across the first section 44 from the first side edge 40 to the second side edge 42. The elastic strands 50 function to cause the first section 44 to securely and snugly contact the back and sides of a wearer's torso and prevent fluid leakage from occurring at or about the waist opening.

As shown in FIG. 1, the elastic strands 50 can be present throughout the entire length $L_2$ of the first section 44. Likewise, if the first section 44 is made from an elastic material, the elastic material can extend the full length $L_2$.

The amount the first section 44 can extend or stretch can vary depending upon the type of disposable absorbent article produced and the size of the person wearing such an article. However, for an incontinence garment designed to be worn by an adult, the first section 44 should be capable of extending in the transverse direction by at least about 25%. Preferably, the first section 44 should be capable of extending in the transverse direction by at least about 50%. More preferably, the first section 44 should be capable of extending in the transverse direction by at least about 75%. Most preferably, the first section 44 should be capable of extending in the transverse direction from between about 75% to about 400%. The first section 44 should also be sized so as to fit around from between about 25% to about 80% of a person's torso when in a non-extended condition. Preferably, the first section 44 should also be sized so as to fit around from between about 30% to about 70% of a person's torso when in a non-extended condition. Most preferably, the first section 44 should also be sized so as to fit around from between about 40% to about 60% of a person's torso when in a non-extended condition. This size dimension for the first section 44 will reduce the need for the material forming it to be stretched to an extreme amount when being fitted around a person's torso.

Referring again to FIGS. 1–3, the back portion 14 has a first fastener 52 and a second fastener 54 secured thereto. Each of the first and second fasteners 52 and 54 are positioned adjacent to one of the first and second side edges 40 and 42, respectively. Each of the first and second fasteners 52 and 54 can be secured by glue, an adhesive, by ultrasonic bonding, by heat, by pressure, by a combination of heat and pressure, by thread, by a mechanical means or by other means known to those skilled in the art. In FIGS. 1–3, the first and second fasteners 52 and 54 are depicted as distinctive, discrete members having a rectangular profile. The first and second fasteners 52 and 54 are shown being located slightly inboard of the respective first and second side edges 40 and 42. The size and shape of the first and second fasteners 52 and 54 can vary. Each of the first and second fasteners 52 and 54 is preferably formed of similar material, although each can be made from a different material, if so desired. The first and second fasteners 52 and 54 can be formed from many different types of materials. For example, the first and second fasteners 52 and 54 can be an adhesive, a co-adhesive, a hook material, a loop material, etc. Preferably, the first and second fasteners 52 and 54 are formed from either a hook material or from a loop material since these materials are readily available and inexpensive.

It should be also be recognized that other types of fastening mechanisms can be used to releasably attach the front and back portions 12 and 14 together. Such other fastening mechanisms can include adhesives, co-adhesives, as well as mechanical fasteners, such as buttons and buttonholes, etc. Those skilled in the art are familiar with the various fastening mechanisms that can be utilized.

The first and second fasteners 52 and 54 are constructed such that they are releasably attachable to the front portion 12 or 12'. For example, at least one of the first and second fasteners 52 and 54 can be made from a hook material so that it can be releasably attached to the front portion 12 or 12' that would be formed from a loop material. It is also possible to form at least one of the first and second fasteners 52 and 54 from a loop material so that it can be releasably attached to the front portion 12 or 12' that would be formed from a hook material. The refastening aspect of this invention allows the wearer to easily remove the absorbent article 10 from his or her torso, for example, to go to the bathroom. The refastenable aspect also allows the wearer to release and adjust the fit of the absorbent article 10 against his or her body as required. For example, if the absorbent article 10 appears to be too loose or too tight, the fasteners 52 and 54 can be released and be readjusted.

Figure 6:
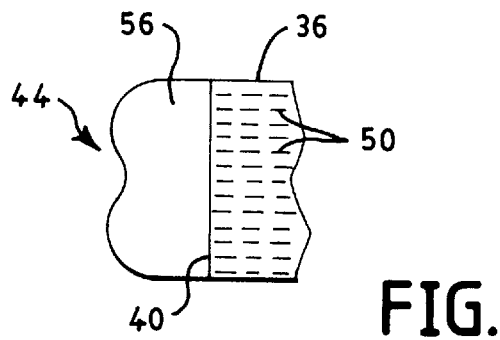
FIG. 6 is a top view of a portion of the left side of said back portion showing an alternative fastener.

Referring now to FIG. 6, an alternative embodiment is shown for a fastener 56 which is secured to the first side edge 40 of the first section 44. The fastener 56 is shown as a separate piece of material securely bonded to the first side edge 40 so as to extend outward therefrom. A similar fastener 56 would be present on the second side edge 42 of the first section 44. As explained above for the first and second fasteners 52 and 54, the fastener 56 can be formed from a hook material, a loop material or from some other kind of material. The fastener 56 can be elastic or non-elastic. The fastener 56 can vary in size and shape and how it is permanently secured onto the back portion 14. Preferably, the fastener 56 is either a hook or loop material that can be releasably attachable to the front portion 12 or 12'. It should be noted that the entire surface of each of the fasteners 56 does not have to be formed from a fastening material. Instead, only a portion of the surface can be the fastening element and the remaining portion of the surface can be formed from a non-fastening material.

Referring now to FIGS. 1 and 7, the second section 46 of the back portion 14 has a length $L_3$ measured perpendicularly from the second end 38 to the line 48 drawn parallel to the first end 36. The length $L_3$ should be equal to or greater than about 1 inch (about 2.5 cm). Preferably, for an adult size garment, the length $L_3$ should range from between about 3 inches to about 10 inches (about 8 cm to about 25 cm). Most preferably, for an adult size garment, the length $L_3$ should range from between about 4 inches to about 8 inches (about 10 cm to about 20 cm).

The second section 46 may or may not contain elastic 50 that extends transversely thereacross. By designing and manufacturing the absorbent article 10 to have a ratio $L_2/L_3$, which ranges from between about 0.1 to about 2, one can improve the body fit of the disposable absorbent article 10. Preferably, the ratio $L_2/L_3$ ranges from between about 0.2 to about 1.6, and more preferably, the ratio $L_2/L_3$ ranges from between about 0.3 to about 1.5. By manufacturing the back portion 14 to this desired ratio, one can also minimize fluid leakage.

The second section 46 has first and second leg elastics 58 and 60 that are aligned adjacent to first and second edges 62 and 64. Preferably, the line 48 will intersect at a point where the first and second edges 62 and 64 meet the first and second side edges 40 and 42, respectively. The first and second leg elastics 58 and 60 can include one or more elastic strands, ribbons, bands or strips that are arranged approximately parallel to the first and second edges 62 and 64, respectively. Preferably, there are from between about 1 to about 6 elongated elastic strands making up each leg elastic 58 and 60. Most preferably, each of the leg elastics 58 and 60 contains three elastic strands. The elastic strands can be aligned parallel to one another. For good results, the leg elastics 58 and 60 should be positioned inward about 1 inch (about 2.5 cm) from the first and second edges 62 and 64, respectively. More preferably, the leg elastics 58 and 60 should be positioned inward about 0.75 inches (about 2 cm) from the first and second edges 62 and 64, respectively. Most preferably, the leg elastics 58 and 60 should be positioned inward about 0.5 inches (about 1.3 cm) from the first and second edges 62 and 64.

The edges 62 and 64 are aligned at an angle to the longitudinal centerline X—X of the absorbent article 10. The cut of the second section is important to obtain the desired fit and functioning of the absorbent article 10. In the planar view of the absorbent article 10, see FIG. 1, the majority (at least 51%) of the side edges of the second section form a substantially linear line. Preferably, the side edges are substantially linear for a length of at least about 70% of the length of the second section. The straight section of the side edges should form an acute angle with the longitudinal centerline X—X. More preferably, each linear line forms an angle of from between about 25 degrees and about 89 degrees, most preferably, each linear line forms an angle of from between about 55 degrees to about 87 degrees and even more preferably, between about 61 degrees and 76 degrees.

The first and second leg elastics 58 and 60 are shown extending from the line 48 to the second end 38 of the back portion 14. One should note that the exact location of the line 48 would dictate whether the leg elastics 58 and 60 are completely contained within the second section 46 or if they extend into the first section 44. The first and second leg elastics 58 and 60 can extend out to the first and second side edges 40 and 42 of the first section 44, if desired. The leg elastics 58 and 60 function to gather the material from which the second section 46 is formed at a location adjacent to the leg openings. The leg openings are formed as the first and second fasteners 52 and 54 are releasably attached to the front portion 12 to form a pant-like article. Various types of elastics can be used to form the leg elastics 58 and 60. The leg elastics 58 and 60 should have a tension of from between about 10 grams to about 400 grams. Preferably, the leg elastics 58 and 60 should have a tension of from between about 50 grams to about 220 grams. More preferably, the leg elastics 58 and 60 should have a tension of from between about 80 grams to about 200 grams.

Referring to FIGS. 1 and 8, the absorbent article 10 also includes the crotch portion 16. The crotch portion 16 connects the front portion 12 to the back portion 14. As noted above, the front portion 12, back portion 14 and the crotch portion 16 can all be part of a single sheet of material. The crotch portion 16 has a first side edge 66 and a second side edge 68 and can have an hourglass, rectangular, square, oval or some other configuration. Each of the side edges 66 and 68 can be straight and aligned parallel or non-parallel to one another. The side edges 66 and 68 can also be curved, arcuate, irregular, convex or concave in shape. Preferably, the side edges 66 and 68 are arcuate in shape with the narrowest distance between the side edges 66 and 68 occurring along the transverse centerline Y—Y. The crotch portion 16 can be a single layer or a laminate, as depicted. Since the crotch portion 16 acts as a baffle to body fluid that is absorbed by the absorbent article 10, it should be liquid-impermeable. If the crotch portion 16 is a laminate, at least one of the layers forming the laminate should be liquid-impermeable. Polypropylene, polyethylene, or any other thermoplastic material works well as a liquid-impermeable layer. Preferably, the crotch portion 16 is a laminate formed from a layer of thermoplastic film and a layer of non-woven material. The non-woven material can be spunbond. Spunbond is a non-woven material manufactured and commercial sold by Kimberly-Clark Corporation having an office at 401 North Lake Street, Neenah, Wis. 54956.

The crotch portion 16 also includes first and second crotch elastics 70 and 72, respectively. The crotch elastics 70 and 72 are located adjacent to the first and second side edges 66 and 68, respectively. The crotch elastics 70 and 72 are preferably contoured to match the profile of the side edges 66 and 68. The crotch elastics 70 and 72 are located inward about 1 inch (about 2.5 cm) of the first and second side edges 66 and 68, respectively. Preferably, the crotch elastics 70 and 72 are located inward about 0.75 inches (about 2 cm) of the first and second side edges 66 and 68, respectively. More preferably, the crotch elastics 70 and 72 are located inward about 0.5 inches (about 1.3 cm) of the first and second side edges 66 and 68, respectively.

The crotch elastics 70 and 72 should have a tension of from between about 10 grams to about 400 grams. Preferably, the crotch elastics 70 and 72 should have a tension of from between about 50 grams to about 220 grams. More preferably, the crotch elastics 70 and 72 should have a tension of from between about 80 grams to about 200 grams.

The crotch elastics 70 and 72 can include one or more elongated elastic strands, ribbons or strips. Preferably, each of said first and second crotch elastics 70 and 72 includes at least two strands of elastics, and more preferably, at least three strands of elastics. The strands of each of the crotch elastics 70 and 72 can be aligned parallel to one another or they can be aligned in a non-parallel relationship, if so desired. A parallel alignment is preferred. The strands of each of the crotch elastics 70 and 72 can be spaced fairly close together, for example, within a millimeter of each other. The exact spacing can be adjusted depending on the size of the article, the width of the crotch portion 16, the strength of the crotch elastics 70 and 72, the material from which the absorbent article 10 is constructed, etc.

Referring to FIGS. 7 and 8, the crotch elastics 70 and 72 can be positioned and secured between the layers 18 and 20 forming the laminate, similar to that shown in FIG. 7. Alternatively, the crotch elastics 70 and 72 can be adhered to an upper surface 74 of the upper layer 18 of the laminate, see FIG. 8. Preferably, the first and second crotch elastics 70 and 72 are bonded to the upper surface 74 of the upper layer 18 by an adhesive.

Referring again to FIGS. 1, 2, 7 and 8, the absorbent article 10 can include a liquid permeable liner 76. The liquid permeable liner 76 is also referred to as a bodyside cover. The liner 76 is not required but the absorbent article 10 will be described as including the liner 76. The liquid permeable liner 76, when present, can be formed from any natural or synthetic material that is liquid permeable. The liquid permeable liner 76 can also be formed from a non-woven material. Spunbond is a good material from which to construct the liquid permeable liner 76.

The bodyside liner 76 can be secured to at least one of the front, back or crotch portions 12, 14 or 16. The bodyside liner 76 is shown being directly attached to the crotch portion 16 in FIG. 8. Alternatively, the bodyside liner 76 can be indirectly attached to the crotch portion 16 via one or more layers. In this case, the intermediate layer would be secured to at least one of the front, back or crotch portions 12, 14 or 16. For example, the bodyside liner 76 could be secured to a liquid-impermeable baffle, that is then adhesively secured to the crotch portion 16.

In FIG. 1, the periphery of the bodyside liner 76 and the periphery of the crotch portion 16 are shown to be coterminous. When the crotch elastics 70 and 72 are positioned on the upper surface 74 of the laminate, see FIG. 8, they can be adhesively secured to the bodyside liner 76 such that they are arranged adjacent to the side edges 66 and 68 of the crotch portion 16.

The absorbent article 10 further includes an absorbent 78 positioned below the liquid permeable liner 76. The absorbent 78 can be in direct contact with the upper layer 18 of the crotch portion 16. The absorbent 78 is designed to absorb body fluid, especially urine and can include one or more layers of absorbent material. The layers can be constructed of similar or different materials. Suitable materials for the absorbent 78 include cellulose, wood pulp fluff, rayon, cotton, and meltblown polymers such as polyester, polypropylene or coform. Coform is a meltblown air-formed combination of meltblown polymers such as polypropylene, and absorbent staple fibers such as cellulose. A preferred material is wood pulp fluff, for it is low in cost, relatively easy to form and has great absorbency. It should be noted that if two or more layers are utilized, that it is not necessary that all the layers be formed from the same material or have the same density.

The absorbent 78 can also be formed from a composite comprised of a hydrophilic material that can be formed from various natural or synthetic fibers, wood pulp fibers, regenerated cellulose or cotton fibers, or a blend of pulp and other fibers. A preferred material is airlaid tissue.

It is also possible and sometimes advantageous to insert a superabsorbent material into the absorbent 78 so as to increase its ability to absorb a large amount of fluid in relation to its own weight. Typical superabsorbents used in absorbent articles such as incontinence garments and diapers can absorb more than 10 times their weight in body fluid. The superabsorbent material can be inserted as particles, fibers or in sheet form. Hydroxyfunctional polymers have been found to be good superabsorbents for disposable absorbent articles. Such superabsorbents are commercially available from The Dow Chemical Company, Stockhausen, Inc., as well as other companies. Two such superabsorbents are DRYTECH® 2035 M and FAVOR® SXM 880. DRYTECH® is a registered trademark of The Dow Chemical Company having an office at 2030 Dow Center, Midland, Mich. 48642. FAVOR® is a registered trademark of Stockhausen, Inc. having an office at 2401 Doyle Street, Greensboro, N.C. 27406. The superabsorbent can be a partially neutralized salt of cross-linked copolymers of polyacrylic acid. Other types of superabsorbent materials known to those skilled in the art can also be used.

Referring now to FIGS. 9 and 10, an absorbent assembly 80 is depicted which includes, from top to bottom, a liquid permeable bodyside liner 76, one or more layers of an absorbent 78, one layer being shown, and a liquid-impermeable baffle 82. The liquid-impermeable baffle 82 can be formed from a thin layer of thermoplastic material such as polyethylene or polypropylene. The baffle 82 can also be formed from other kinds of liquid-impermeable material. Preferably, the baffle 82 is formed from a liquid-impermeable film. It should be noted that the baffle 82 could be formed from a laminate wherein at least one of the layers is liquid-impermeable.

In the absorbent assembly 80, the crotch elastics 70 and 72 are sandwiched between the liner 76 and the baffle 82. The crotch elastics 70 and 72 can be held in place by a glue, an adhesive, by ultrasonics, by heat, by pressure, by a combination of heat and pressure, or by some other bonding mechanism known to those skilled in the art. It is also possible to secure the crotch elastics 70 and 72 to the lower or exterior surface of the baffle 82 if desired. For good results, the crotch elastics 70 and 72 should be positioned within about 1 inch (about 2.5 cm) from the respective side edge 66 and 68. More preferably, the crotch elastics 70 and 72 should be positioned within about 0.75 inches (about 2 cm) from the respective side edge 66 and 68. Most preferably, the crotch elastics 70 and 72 should be positioned within about 0.5 inches (about 1.3 cm) from the respective side edge 66 and 68.

The absorbent assembly 80 can be placed or positioned on or over the crotch portion 16 of the absorbent article 10 and can be retained in place by an adhesive or some other type of fastener. Since the baffle 82 is liquid-impermeable, the crotch portion 16 would not have to be constructed from a liquid-impermeable material. The absorbent assembly 80 can be either permanently or releasably secured to at least one of the front, back or crotch portions 12, 14 or 16 of the absorbent article 10. Preferably, the absorbent assembly 80 is secured to the crotch portion 16 by an adhesive. Alternatively, the absorbent assembly 80 can actually serve as the front and crotch portions, 12 and 16 respectively, of the absorbent article 10.

Figure 11:
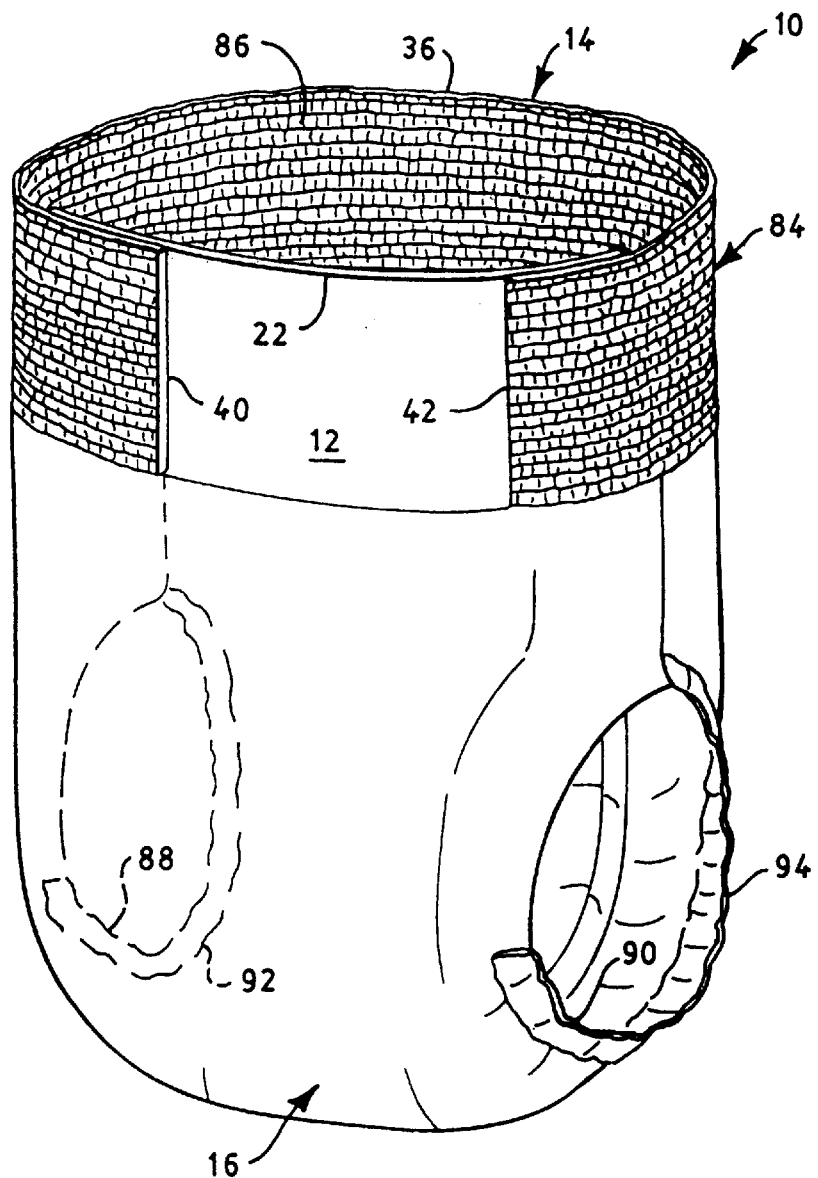
FIG. 11 is a perspective view of the "in use" configuration of the absorbent article shown in FIG. 1 once the first and second lateral section and the back portion are secured together.

Referring now to FIGS. 1 and 11, the first and second fasteners 52 and 54 are releasably attached to the front portion 12 to form a pant-like article 84. The pant-like article 84 has a waist-opening 86 and a pair of first and second leg openings 88 and 90. The leg elastic 58, the crotch elastic 70 and possibly the elastic first section 44 can cooperate to form gathers 92 around the first leg opening 88. Likewise, the leg elastic 60, the crotch elastic 72, and possibly the elastic first section 44 can cooperate to form gathers 94 around the second leg opening 90. It should be noted that the absorbent article 10 could be sold in either the flat, unassembled condition, as shown in FIG. 1, or in the assembled condition, as is shown in FIG. 11.

Referring again to FIG. 1, the back portion 14 of the disposable absorbent article 10 has been described with reference to a first section 44 and a second section 46. The first section 44 has a length $L_2$ and the second section 46 has a length $L_3$, both measured parallel to the longitudinal central axis X—X. The combination of the length $L_2$ and the length $L_3$ equals a new length $L_4$. The length $L_4$ should range from between about 3 inches (about 7.5 cm) to about 25 inches (about 64 cm. Preferably, for an adult size garment, the length $L_4$ should range from between about 7 inches to about 17 inches (about 18 cm to about 43 cm). Most preferably, for an adult size garment, the length $L_4$ should range from between about 10 inches to about 15 inches (about 25 cm to about 38 cm).

In addition, the absorbent article 10 has an overall length $L_5$ measured perpendicularly from the first end 22 of the front portion 12 to the first end 36 of the back portion 14. The length $L_5$ should range from between about 10 inches (about 25 cm) to about 45 inches (about 114 cm). Preferably, for an adult size garment, the length $L_5$ should range from between about 20 inches (about 51 cm) to about 40 inches (about 102 cm). Most preferably, for an adult size garment, the length $L_5$ should range from between about 30 inches (about 76 cm) to about 35 inches (about 89 cm).

A ratio $L_4/L_5$ can be established which ranges from between about 0.1 to about 0.5. Preferably, the ratio $L_4/L_5$ ranges from between about 0.2 to about 0.5 and more preferably, the ratio $L_4/L_5$ ranges from between about 0.3 to about 0.4. By designing and manufacturing the absorbent article 10 to fit within the values established for the ratio $L_4/L_5$, one can be confident that the absorbent article 10 will exhibit improved body fit and be less likely to leak body fluid.

Figure 12:
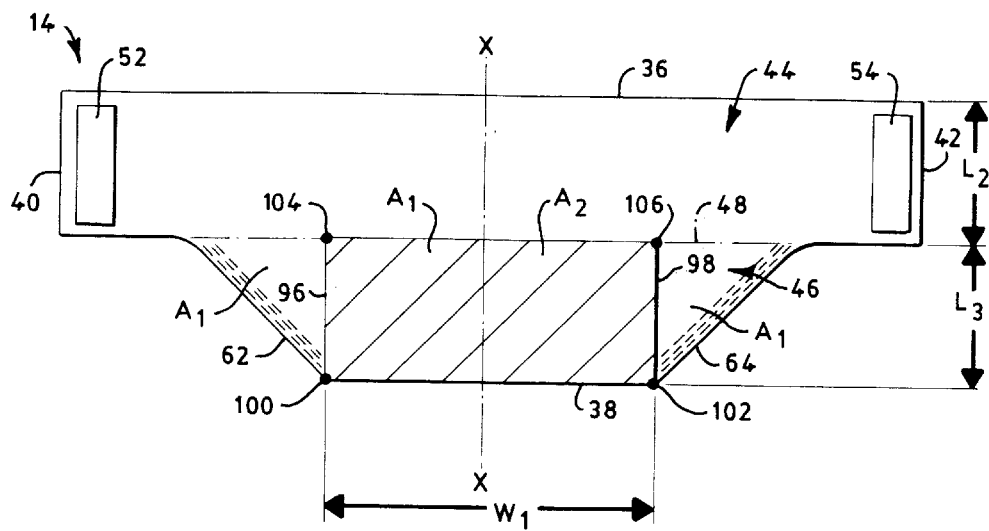
FIG. 12 is a top view of the back portion of the absorbent article shown in FIG. 1 with the elastic removed for clarity and showing one way to measure a ratio $A_1/A_2$ for the second section in order to obtain improved body fit.

Referring now to FIG. 12, the back portion 14 of the refastenable disposable absorbent article 10 is depicted with the elastic 50 removed for clarity of discussion only. The back portion 14, as described above, has a first section 44 and a second section 46. The first section 44 has a length $L_2$ that is equal to or greater than about 2 inches (about 5 cm) and the second section 46 has a length $L_3$ that is equal to or greater than about 1 inch (about 2.5 cm). The second section 46 includes a first area $A_1$ and a second area $A_2$. The first area $A_1$ is bounded by the second end 38, the line 48 drawn parallel to the first end 36, and the first and second edges 62 and 64. In essence, the first area $A_1$ represents the total area of the second section 46. The second area $A_2$ is depicted as the cross hatched area bounded by first and second lines 96 and 98, the second end 38, and the line 48 drawn parallel to the first end 36. The first and second lines 96 and 98 are drawn perpendicular to the second end 38 at points 100 and 102 where the first and second edges 62 and 64 intersect the second end 38. The first and second lines 96 and 98 extend vertically upward and intersect the line 48 at points 104 and 106, respectively. It has been found that if one divides the first area $A_1$ by the second area $A_2$, a ratio $A_1/A_2$ is established. If this ratio $A_1/A_2$ is maintained within a certain limited range, one can manufacture a disposable absorbent article 10 that exhibits improved body fit in the buttocks region of the wearer. Such improved body fit reduces the likelihood of fluid leakage from occurring which is of utmost importance to a consumer of such products.

The first area $A_1$ should be equal to or greater than about 175 $cm^2$. Preferably, for an adult size garment, the first area $A_1$ ranges from between about 400 $cm^2$ to about 1500 $cm^2$. More preferably, for an adult size garment, the first area $A_1$ ranges from between about 500 $cm^2$ to about 1200 $cm^2$. Most preferably, for an adult size garment, the first area $A_1$ ranges from between about 600 $cm^2$ to about 1100 $cm^2$. The second area $A_2$ should be equal to or greater than about 135 $cm^2$. The ratio $A_1/A_2$ should range from between about 1.3 to about 3.5. Preferably, the ratio $A_1/A_2$ should range from between about 1.7 to about 2.5, and more preferably, the ratio $A_1/A_2$ should range from between about 2.0 to about 2.3.

It should be noted that the first and second lines 96 and 98 are aligned parallel to one another and are spaced apart a distance denoted as $W_1$. $W_1$ represents the width of the second area $A_2$. The width $W_1$ should be equal to or greater than about 4 inches (about 10 cm). Preferably, the width $W_1$ should range from between about 5 inches (about 13 cm) to about 15 inches (about 38 cm), and more preferably, the width $W_1$ should range from between about 6 inches (about 15 cm) to about 11 inches (about 28 cm). The dimension $W_1$ can vary depending upon the type and size of the absorbent article, as well as the age and physical size of the wearer that the absorbent article is designed to be worn by. If the absorbent article is sized to be worn by an infant, the dimension $W_1$ will be less than if the absorbent article was designed to be worn by a toddler or by an adult. The gender of the wearer can also affect the dimension $W_1$.

Figure 13:
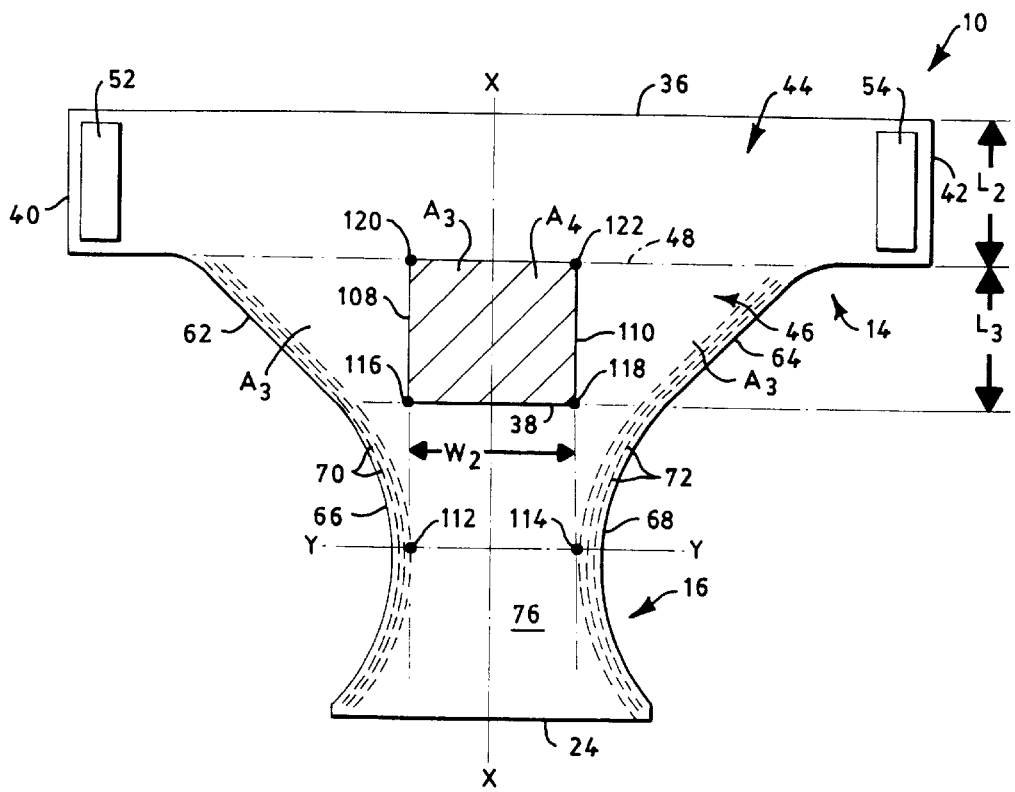
FIG. 13 is a top view of the back portion and crotch portion of the absorbent article shown in FIG. 1 with the elastic removed for clarity and showing an alternative way to measure a ratio $A_3/A_4$ for the second section in order to obtain improved body fit.

Referring to FIG. 13, the back portion 14 and the crotch portion 16 of the absorbent article 10 are depicted with the elastic 50 removed from the back portion 14 for clarity of discussion only. The crotch portion 16 is joined at one end to the second end 38 of the back portion 14. The crotch portion 16 has first and second side edges 66 and 68 and first and second crotch elastics 70 and 72 positioned adjacent to the first and second side edges 66 and 68, respectively. The back portion 14 has a first section 44 and a second section 46. The first section 44 has a length $L_2$ that is equal to or greater than about 2 inches (about 5 cm) and the second section 70 has a length $L_3$ that is equal to or greater than about 1 inch (about 2.5 cm). The second section 46 includes a first area $A_3$ and a second area $A_4$. The first area $A_3$ is bounded by the second end 38, the line 48 drawn parallel to the first end 36, and the first and second edges 62 and 64. In essence, the first area $A_3$ represents the total area of the second section 46. The second area $A_4$ is depicted as the crosshatched area bounded by first and second lines 108 and 110, the second end 38, and the line 48 drawn parallel to the first end 36. The first and second lines 108 and 110 are drawn tangential to the first and second crotch elastics 70 and 72 at points 112 and 114 where the first and second crotch elastics 70 and 72 are spaced closest together. Another way of stating this is that the first and second lines 108 and 110, respectively, are aligned tangentially to the inner most elastic strand of each of the first and second crotch elastics 70 and 72. For a symmetrically shaped article 10, this will occur on the transverse central axis Y—Y.

The first and second lines 108 and 110 extend vertically upward toward the first end 36 and intersect both the second end 38 at points 116 and 118, and the line 48 drawn parallel to the first end 36 at points 120 and 122. The crosshatched area bounded by the points 116, 118, 120 and 122 represent the second area $A_4$. It has been found that if one divides the first area $A_3$ by the second area $A_4$, that a ratio $A_3/A_4$ is established. If this ratio $A_3/A_4$ is maintained within a certain limited range, one can manufacture an absorbent article that exhibits improved body fit in the buttocks region of the wearer. Such improved body fit reduces the likelihood of fluid leakage from occurring which is of utmost importance to a disposable absorbent article.

The first area $A_3$ should be equal to or greater than about 160 $cm^2$. Preferably, the first area $A_3$ should range from between about 400 $cm^2$ to about 1500 $cm^2$. More preferably, the first area $A_3$ should range from between about 500 $cm^2$ to about 1200 $cm^2$, and most preferably, the first area $A_3$ ranges from between about 600 $cm^2$ to about 1100 $cm^2$. The second area $A_4$ should be equal to or greater than about 105 $cm^2$. The ratio $A_3/A_4$ should range from between about 1.5 to about 5.0. Preferably, the ratio $A_3/A_4$ should range from between about 2.5 to about 4.0, and more preferably, the ratio $A_3/A_4$ should range from between about 3.0 to about 3.7.

It should be noted that the first and second lines 108 and 110 are aligned parallel to one another and are spaced apart a distance denoted as $W_2$. $W_2$ represents the width of the second area $A_4$. The width $W_2$ should be equal to or greater than about 2 inches (about 5 cm). Preferably, the width $W_2$ should range from between about 3 inches (about 8 cm) to about 7 inches (about 18 cm), and more preferably, the width $W_2$ should range from between about 4 inches (about 10 cm) to about 6 inches (about 15 cm). The dimension $W_2$ can vary depending upon the type and size of absorbent article, as well as the age and physical size of the wearer that the absorbent article is designed to be worn by. If the absorbent article is sized to be worn by an infant, the dimension $W_2$ will be less than if the absorbent article was designed to be worn by a toddler or by an adult. The gender of the wearer can also affect the dimension $W_2$.

While the invention has been described in conjunction with several specific embodiments, it is to be understood that many alternatives, modifications and variations will be apparent to those skilled in the art in light of the aforegoing description. Accordingly, this invention is intended to embrace all such alternatives, modifications and variations that fall within the spirit and scope of the appended claims.

We claim:

1. An absorbent article having a longitudinal axis comprising:
    a) a front portion having a first end and a second end;
    b) a crotch portion joined at one end to said front portion, and joined at an opposite end to a back portion; said crotch portion having a first side edge, a first crotch elastic positioned adjacent to said first side edge, a second side edge, and a second crotch elastic positioned adjacent to said second side edge; each of said first and second side edges of said crotch portion having an end point adjacent said back portion; said end points located where a line drawn parallel to said longitudinal axis, at a maximum distance transversely from said longitudinal axis, passes through said first and second side edges of said crotch portion at least twice;
    c) said back portion being divided into a first section and a second section; said first section bounded by a first end, a line drawn parallel to said first end, a first side edge, and a second side edge, said first section being extendable in a traverse direction; said second section bounded by said line drawn parallel to said first end, a second end, a first edge, and a second edge defining a first area $A_3$; said line drawn parallel to said first end intersecting a pair of corners where said first and second side edges of said first section intersect with said first and second edges of said second section; said second end parallel to said first end and intersecting said end points where said first and second side edges of said crotch portion intersect with said first and second edges of said second section; said first section having a length $L_2$ measured perpendicularly from said first end to said line drawn parallel thereto, said length $L_2$ being equal to or greater than about 2 inches; said second section having a length $L_3$ measured perpendicularly from said line drawn parallel to said first end to said second end, said length $L_3$ being equal it or greater than about 1 inch; said second section having a second area $A_4$ defined by said line drawn parallel to said first end, said second end, and by a first line and a second line, said first and second lines being drawn tangential to said first and second crotch elastics at points where said first and second crotch elastics are spaced closest together, said first and second lines intersecting with said second end and with said line drawn parallel to said first end; and said back portion having a ratio $A_3/A_4$ ranging from between about 2.5 to about 4.0;
    d) first and second fasteners secured to said back portion; and
    e) an absorbent secured to at least one of said front, back or crotch portions, and each of said first and second fasteners being releasably attached to said front portion to form a pant-like article having a waist opening and a pair of leg openings.

2. The absorbent article of claim 1 wherein said first section is elastic.

3. The absorbent article of claim 1 wherein said first section is constructed from an elastic material.

4. The absorbent article of claim 1 wherein said first section contains multiple elastic strands that extend transversely thereacross from a first side edge to a second side edge.

5. The absorbent article of claim 1 wherein said first section is capable of extending in the transverse direction by at least about 25%.

6. The absorbent article of claim 5 wherein said first section is capable of extending in the transverse direction by at least about 50%.

7. The absorbent article of claim 6 wherein said first section is capable of extending in the transverse direction by at least about 75%.

8. The absorbent article of claim 1 wherein at least one of said first and second fasteners is formed from a hook material that is releasably attached to said front portion which is formed from a loop material.

9. The absorbent article of claim 1 wherein at least one of said first and second fasteners is formed from a loop material that is releasably attached to said front portion which is formed from a hook material.

10. An absorbent article having a longitudinal axis comprising:
    a) a front portion having a first end and a second end;
    b) a crotch portion joined at one end to said front portion, and joined at an opposite end to a back portion; said crotch portion having a first side edge, a first crotch elastic positioned adjacent to said first side edge, a second side edge, and a second crotch elastic positioned adjacent to said second side edge; each of said first and second side edges of said crotch portion having an end point adjacent said back portion; said end points located where a line drawn parallel to said longitudinal axis, at a maximum distance transversely from said longitudinal axis, passes through said first and second side edges of said crotch portion at least twice;
    c) said back portion being divided into a first section and a second section; said first section bounded by a first end, a line drawn parallel to said first end, a first side edge, and a second side edge, said first section being extendable in a traverse direction; said second section bounded by said line drawn parallel to said first end, a second end, a first edge, and a second edge defining a first area $A_3$; said line drawn parallel to said first end intersecting a pair of corners where said first and second side edges of said first section intersect with said first and second edges of said second section; said second end parallel to said first end and intersecting said end points where said first and second side edges of said crotch portion intersect with said first and second edges of said second section; said first section having a length $L_2$ measured perpendicularly from said first end to said line drawn parallel thereto, said length $L_2$ being between about 3 inches to about 7 inches; said second section having a length $L_3$ measured perpendicularly from said line drawn parallel to said first end to said second end, said length $L_3$ being between about 3 inches to about 10 inches; said second section having a second area $A_4$ defined by said line drawn parallel to said first end, said second end, and by a first line and a second line, said first and second lines being drawn tangential to said first and second crotch elastics at points where said first and second crotch elastics are spaced closest together, said first and second lines intersecting with said second end and with said line drawn parallel to said first end; and said back portion having a ratio $A_3/A_4$ ranging from between about 2.5 to about 4.0;
    d) first and second fasteners secured to said first section;
    e) a liquid permeable liner secured to at least one of said front, back or crotch portions; and f) an absorbent positioned below said liner, and each of said first and second fasteners being releasably attached to said front portion to form a pant-like article having a waist opening and a pair of leg openings.

11. The absorbent article of claim 10 wherein said first section is elastic.

12. The absorbent article of claim 10 wherein at least one of said first and second fasteners is formed from a hook material that is releasably attached to said front portion which is formed from a loop material.

13. The absorbent article of claim 10 wherein at least one of said first and second fasteners is formed from a loop material that is releasably attached to said front portion which is formed from a hook material.

14. The absorbent article of claim 10 wherein said first section contains multiple elastic strands that extend transversely thereacross from said first side edge to said second side edge, and said first section is capable of extending in the transverse direction by at least about 25%.

15. An absorbent article having a longitudinal axis comprising:

a) a front portion having a first end and a second end;

b) a crotch portion joined at one end to said front portion, and joined at an opposite end to a back portion; said crotch portion having a first side edge, a first crotch elastic positioned adjacent to said first side edge, a second side edge, and a second crotch elastic positioned adjacent to said second side edge; each of said first and second side edges of said crotch portion having an end point adjacent said back portion; said end points located where a line drawn parallel to said longitudinal axis, at a maximum distance transversely from said longitudinal axis, passes through said first and second side edges of said crotch portion at least twice;

c) said back portion being divided into a first section and a second section; said first section bounded by a first end, a line drawn parallel to said first end, a first side edge, and a second side edge, said first section being extendable in a traverse direction; said second section bounded by said line drawn parallel to said first end, a second end, a first edge, and a second edge defining a first area $A_3$, said first area $A_3$ being equal to or greater than about 160 cm$^2$; said line drawn parallel to said first end intersecting a pair of corners where said first and second side edges of said first section intersect with said first and second edges of said second section; said second end parallel to said first end and intersecting said end points where said first and second side edges of said crotch portion intersect with said first and second edges of said second section; said first section having a length $L_2$ measured perpendicularly from said first end to said line drawn parallel thereto, said length $L_2$ being equal to or greater than about 2 inches; said second section having a length $L_3$ measured perpendicularly from said line drawn parallel to said first end to said second end, said length $L_3$ being equal to or greater than about 1 inch; said second section having a second area $A_4$ defined by said line drawn parallel to said first end, said second end, and by a first line and a second line, said first and second lines being drawn tangential to said first and second crotch elastics at points where said first and second crotch elastics are spaced closest together, said first and second lines intersecting with said second end and with said line drawn parallel to said first end; and said back portion having a ratio $A_3/A_4$ ranging from between about 3.0 to about 3.7;

d) first and second fasteners secured to said first section;

e) a liquid permeable liner secured to at least one of said front, back or crotch portions; and d) an absorbent positioned below said liner, and each of said first and second fasteners being releasably attached to said front portion to form a pant-like article having a waist opening and a pair of leg openings.

16. The absorbent article of claim 15 wherein $A_3$ ranges from between about 400 cm$^2$ to about 1500 cm$^2$.

17. The absorbent article of claim 15 wherein at least one of said first and second fasteners is formed from a hook material that is releasably attached to said front portion which is formed from a loop material.

18. The absorbent article of claim 15 wherein at least one of said first and second fasteners is formed from a loop material that is releasably attached to said front portion which is formed from a hook material.

19. The absorbent article of claim 15 wherein said first section contains multiple elastic strands that extend transversely thereacross from said first side edge to said second side edge, and said first section is capable of extending in the transverse direction by at least about 25%.

20. The absorbent article of claim 15 wherein first section is capable of extending in the transverse direction by at least about 50%.

* * * * *